United States Patent [19]
Palmaz et al.

[11] Patent Number: 5,571,170
[45] Date of Patent: Nov. 5, 1996

[54] METHOD AND APPARATUS FOR BILATERAL INTRA-AORTIC BYPASS

[75] Inventors: Julio C. Palmaz, San Antonio, Tex.; Jean C. LaBorde, Montpellier, France

[73] Assignee: Expandable Grafts Partnership, San Antonio, Tex.

[21] Appl. No.: 199,119

[22] Filed: Feb. 22, 1994

Related U.S. Application Data

[62] Division of Ser. No. 818,052, Jan. 8, 1992, Pat. No. 5,316,023.

[51] Int. Cl.$^6$ ............................................. A61F 2/06
[52] U.S. Cl. ..................... 623/1; 623/11; 623/12; 606/108; 606/155
[58] Field of Search ..................... 623/1, 11–12, 623/66, 900; 606/108, 153, 155, 156, 191, 192, 194, 195

[56] References Cited

U.S. PATENT DOCUMENTS

| | | | |
|---|---|---|---|
| 5,078,726 | 1/1992 | Kreamer | 623/12 |
| 5,123,917 | 6/1992 | Lee | 623/11 |
| 5,135,536 | 8/1992 | Hillstead | 623/1 |
| 5,195,984 | 3/1993 | Schatz | 623/1 |
| 5,197,976 | 3/1993 | Herweck et al. | 623/1 |
| 5,219,355 | 6/1993 | Parodi et al. | 606/191 |
| 5,316,023 | 5/1994 | Palmaz et al. | 128/898 |

*Primary Examiner*—David H. Willse
*Assistant Examiner*—P. Zuttarelli
*Attorney, Agent, or Firm*—Ben D. Tobor

[57] ABSTRACT

A bilateral intra-aortic bypass graft and method and apparatus for repairing an abdominal aortic aneurysm includes two tubular grafts which are intraluminally delivered to the aorta and secured to the aorta by the expansion and deformation of two expandable and deformable tubular members.

49 Claims, 4 Drawing Sheets

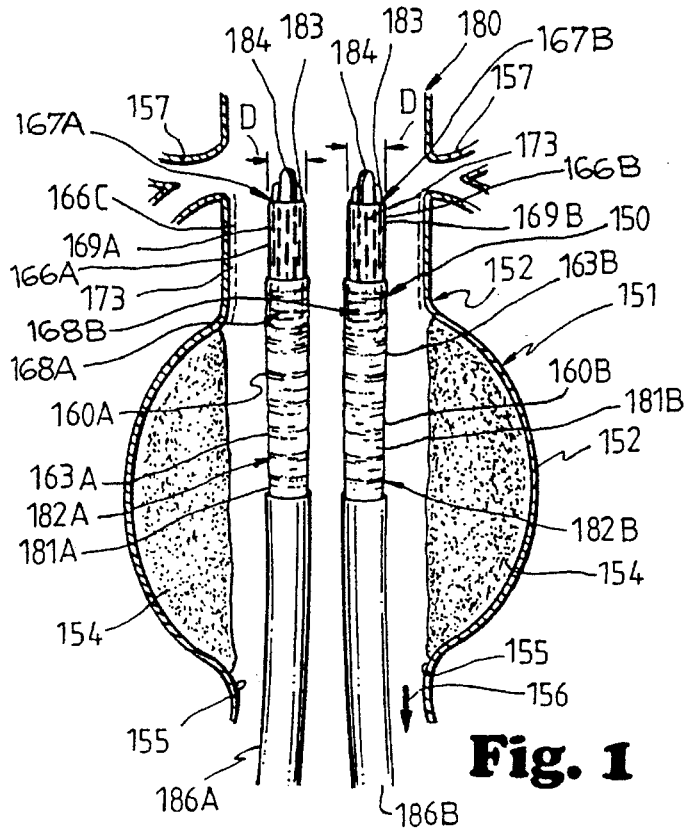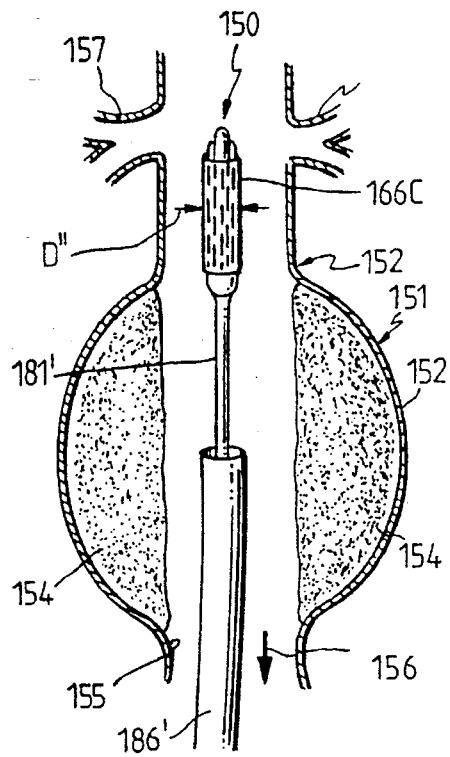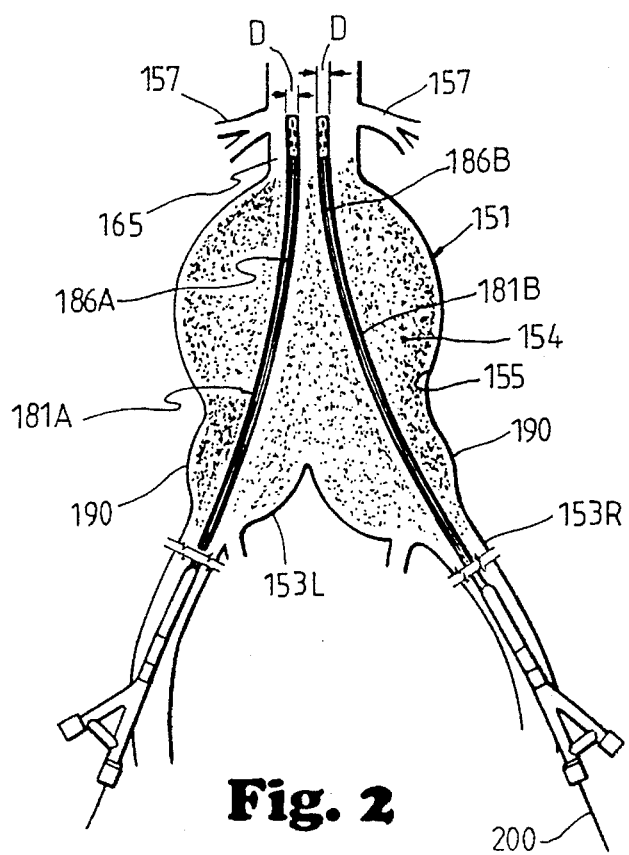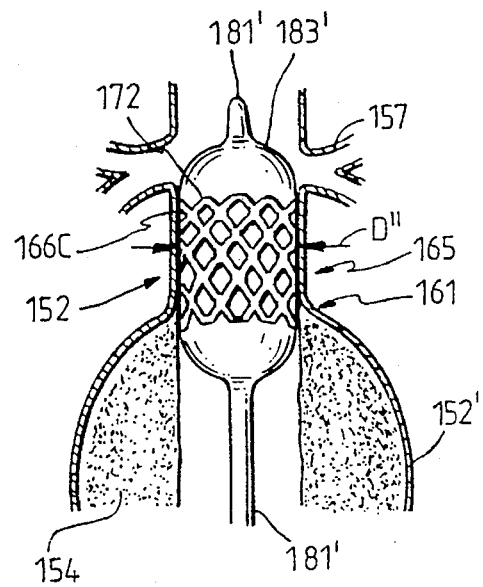
Fig. 1
Fig. 3
Fig. 2
Fig. 4

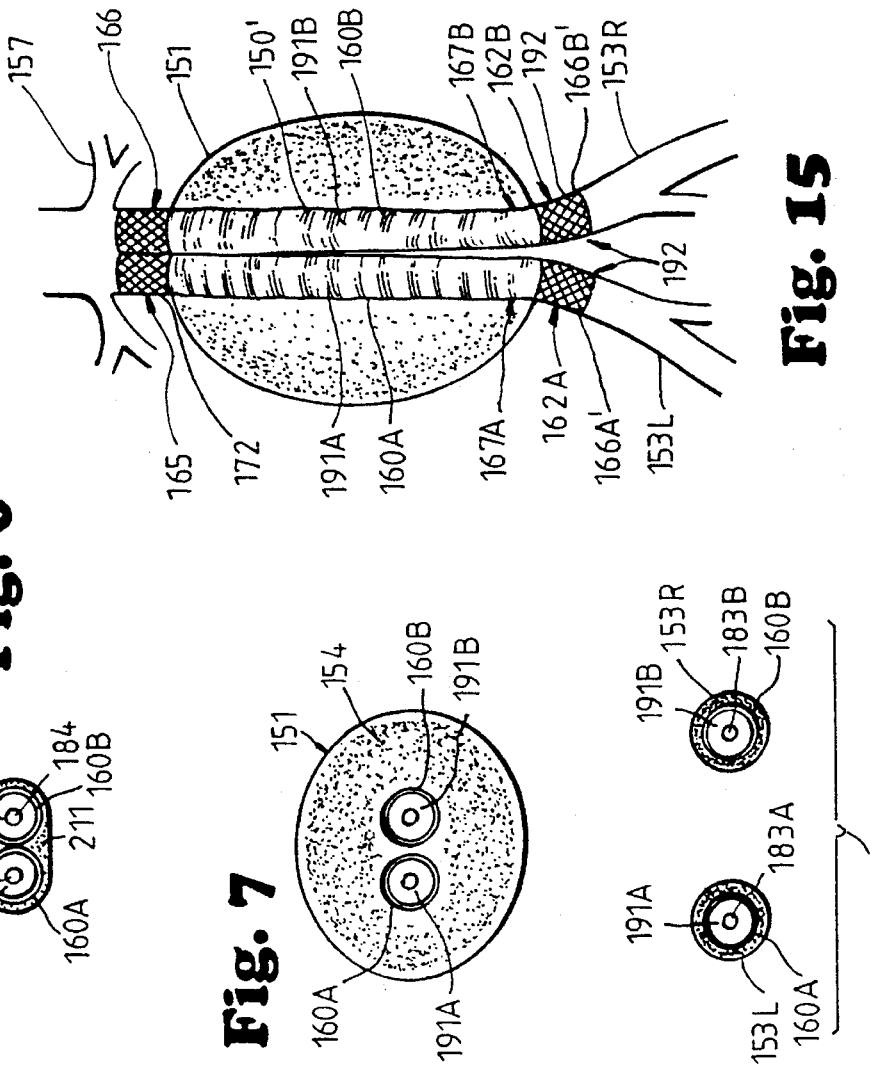

METHOD AND APPARATUS FOR BILATERAL INTRA-AORTIC BYPASS

This is a division, of application Ser. No. 07/818,052, filed Jan. 8, 1992 now U.S. Pat. No. 5,316,023.

BACKGROUND OF THE INVENTION

1. Field of the Invention

The invention relates to a bilateral intra-aortic bypass graft for intraluminal delivery, and a method and apparatus for repairing an abdominal aortic aneurysm.

2. Description of the Prior Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the arteriosclerotically diseased aorta, for example, below the kidneys. When left untreated, the aneurysm will eventually cause rupture of the sac with ensuing fatal hemorrhaging in a very short time. High mortality associated with the rupture has led to the present state of the art and the transabdominal surgical repair of abdominal aortic aneurysms. Surgery involving the abdominal wall, however, is a major undertaking with associated high risks. There, is considerable mortality and morbidity associated with this magnitude of surgical intervention, which in essence involves replacing the diseased and aneurysmal segment of blood vessel with a prosthetic device which typically is a synthetic tube, or graft, usually fabricated of either DACRON®, TEFLON®, or other suitable material.

To perform the surgical procedure, requires exposure of the aorta through an abdominal incision, which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta, is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aorta aneurysm, the survival rate of treated patients is markedly higher than if the surgery is performed after the aneurysm ruptures, although the mortality rate is still quite high. If the surgery is performed prior to the aneurysm rupturing, the mortality rate is typically less than 5%. Conventional surgery performed after the rupture of the aneurysm is significantly higher, one study reporting a mortality rate of 66.7%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate, are: the extended recovery period associated with such surgery; difficulties in suturing the graft, or tube, to the aorta; the loss of the existing thrombosis to support and reinforce the graft; the unsuitability of the surgery for many patients having abdominal aortic aneurysms; and the problems associated with the performing the surgery on an emergency basis after the aneurysm has ruptured. As to the extent of recovery, a patient can expect to spend form 1 to 2 weeks in the hospital after the surgery, a major portion of which is spent in the intensive care unit, and a convalescence period at home from 2 to 3 months, particularly if the patient has other illness such as heart, lung, liver, and/or kidney disease, in which case the hospital stay is also lengthened. Since the graft must be secured, or sutured, to the remaining portion of the aorta, it is many times difficult to perform the suturing step because of thrombosis present on the remaining portion of the aorta, and that remaining portion of the aorta wall may many times be friable, or easily crumbled.

Since the thrombosis is totally removed in the prior art surgery, the new graft does not have the benefit of the previously existing thrombosis therein, which could be utilized to support and reinforce the graft, were the graft to be able to be inserted within the existing thrombosis. Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such surgery, which is considered major surgery. Such patients have difficulties in surviving the operation. Lastly, once the aneurysm has ruptured, it is difficult to perform a conventional surgery on an expedited basis because of the extent of the surgery.

It has been previously proposed to repair abdominal aortic aneurysms by intraluminal delivery of an aortic graft disposed upon a catheter, and securing the graft within the aorta by expansion and deformation of an expandable deformable member associated with the graft by expanding and inflating a portion of the catheter which contacts the tubular member. Because of the relatively large diameter of the catheter and associated graft necessary for implantation within the aorta, some difficulties have been sometimes encountered, such as spasms associated with the access body vessel such as the femoral artery. Additional problems sometimes encountered with this method or repairing an abdominal aortic aneurysm have been kinking and/or twisting of the flexible, collapsible graft during and/or after implantation of the graft.

Accordingly, prior to the development of the present invention, there has been no bilateral intra-aortic bypass graft for intraluminal delivery, or method and apparatus for repairing an abdominal aortic aneurysm, which: does not have a relatively high morbidity and mortality rate; does not have an extended recovery period; does not require suturing the graft to the remaining aorta wall; permits the existing thrombosis therein to support and reinforce the graft; is suitable for older patients with chronic illnesses; is less susceptible to kinking and/or twisting of the graft; and is able to use a smaller diameter delivery system. Therefore, the art has sought a bilateral intra-aortic bypass graft for intraluminal delivery, and method and apparatus for repairing an abdominal aortic aneurysm which is believed to: not have a high morbidity and mortality rate; does not require an abdominal incision and general anesthesia; not require an extended recovery period; not require suturing the graft to the remaining aortic wall; permit the existing aortic wall and thrombosis therein to be retained to reinforce and support the aortic graft; be suitable for patients having other chronic illnesses; be less susceptible to kinking and/or twisting of the graft and permit the use of a smaller diameter delivery system.

SUMMARY OF THE INVENTION

In accordance with the invention, the foregoing advantages have been achieved through the method and apparatus for bilateral intra-aortic graft of the present invention. The method for repairing an abdominal aortic aneurysm in an aorta having two iliac arteries associated therewith may include the steps of: connecting a first tube to a first expandable and deformable, tubular member; connecting a second tube to a second expandable and deformable, tubular member; disposing the first tube and first tubular member upon a first catheter, disposing the second tube and second tubular member upon a second catheter, each catheter having an expandable, inflatable portion with the tubular members disposed upon the expandable, inflatable portions; intraluminally delivering the first and second tubes, tubular members, and catheters to the aorta and disposing at least a portion of each tube within the abdominal aortic aneurysm; and expanding the expandable, inflatable portion of each catheter to expand and deform the tubular members to force the tubular members radially outwardly into contact with the aorta and each other, to secure the tubular members and a least a portion of each tube within the aorta, whereby the tubes provide a bilateral fluid passageway through the abdominal aortic aneurysm.

Another feature of the present invention may include the step of simultaneously expanding the expandable, inflatable portions of each catheter. An additional feature of the present invention is that the first and second tubes may each have first and second ends, the first end of each tube being connected to a tubular member and being disposed within the aorta; and the second end of the first tube may be disposed within one of the iliac arteries, and the second end of the second end may be disposed within the other iliac artery.

A further feature of the present invention is that a third expandable and deformable, tubular member may be connected to the second end of the first tube; a fourth expandable and deformable, tubular member may be connected to the second end of the second tube; and the third and fourth tubular members are expanded and deformed to force the third and fourth tubular members radially outwardly into contact with an iliac artery by the expansion of the expandable, inflatable portion of each catheter associated with each tube. Another feature of the present invention may include the steps of forming each tube of a plurality of expandable and deformable, tubular members, each tubular member having a longitudinal axis, by aligning the plurality of tubular members with their longitudinal axes being substantially parallel with other, each tubular member being detached, and spaced apart, from adjacent tubular members; and embedding the plurality of tubular members within a layer of deformable; and expandable plastic material. The plastic material may be silicone, polytetrafluoroethylene, expanded polytetrafluoroethylene, or expanded polyurethane.

An additional feature of the present invention may include the step of simultaneously expanding the expandable, inflatable portion of each catheter to simultaneously expand and deform the first and second tubular members and the plurality of tubular members of each tube which are embedded in the deformable and expandable plastic material. A further feature of the present invention may include the step of connecting the first and second tubular members to the first and second tubes by embedding a portion of the second ends of the first and second tubular members in the deformable and expandable plastic material of the tube to which it is to be connected.

A further feature of the present invention may include the steps of: disposing a fifth expandable and deformable tubular member upon a third catheter having an expandable, inflatable portion, with the fifth tubular member being disposed upon the expandable, inflatable portion; intraluminally delivering the fifth tubular member and third catheter to the aorta; expanding the expandable, inflatable portion of the third catheter to expand and deform the fifth tubular member to force the third tubular member radially outwardly into a connect with the aorta to secure the fifth tubular member within the aorta; the foregoing steps being conducted prior to the intraluminal delivery of the first and second tubes, tubular members, and catheters, whereupon the simultaneous expansion of the expandable, inflatable portions of the first and second catheters, the first and second tubular members are expanded and deformed radially outwardly to connect with the fifth tubular member and each other, to secure the first and second tubular members within the aorta and within the fifth tubular member.

An additional feature of the present invention may include the steps of forming each tube of a plurality of expandable and deformable, tubular members, each tubular member having a longitudinal axis, by aligning the plurality of tubular members with their longitudinal axes being substantially parallel with other, each tubular member being spaced apart from adjacent tubular members with a single, flexible connector member being disposed between adjacent tubular members; and embedding the plurality of tubular members within a layer of deformable and expandable plastic material.

In accordance with the invention, the foregoing advantages have also been achieved through the present bilateral intra-aortic bypass graft for intraluminal delivery to repair an abdominal aortic aneurysm in an aorta having two iliac arteries associated therewith. This aspect of the present invention includes: a first tube having first and second ends and a wall surface disposed between the two ends, at least a portion of the first tube adapted to be disposed within the abdominal aortic aneurysm; a second tube having first and second ends and a wall surface disposed between the two ends, at least a portion of the second tube adapted to be disposed within the abdominal aortic aneurysm; and means for securing the first ends of the first and second tubes to the aorta, the securing means including first and second tubular members, each tubular member having first and second ends, the first tube being connected to the first tubular member and the second tube being connected to the second tubular member, the tubular members having a first diameter which permits intraluminal delivery of the tubular members and tubes into the aorta and the tubular members having a second, expanded and deformed diameter, with at least a portion of the first and second tubular members in an abutting relationship, upon the application from the interior of the tubular members of a radially, outwardly extending force, the second diameter being variable and dependent upon the amount of force applied to the tubular member, whereby the tubular members may be expanded and deformed to secure the first ends of the tubular members to the aorta and a bilateral fluid passageway is formed within the abdominal aorta aneurysm.

Another feature of the present invention is that at least a portion of the first and second tubes are in an abutting relationship with each other when the first and second tubular members have their second, expanded and deformed diameter. An additional feature of the present invention is that a third expandable and deformable tubular member may be connected to the second end of the first tube; a fourth expandable and deformable tubular member may be connected to the second end of the second tube; and the third and fourth tubular members may be expanded and deformed to force the third and fourth tubular members radially outwardly into contact with an iliac artery by the expansion of the expandable, inflatable portion of each catheter associated with each tube.

A further feature of the present invention is that each tube may be formed of a plurality of expandable and deformable, tubular members, each tubular member having a longitudinal axis, the plurality of tubular members being aligned with their longitudinal axes being substantially parallel with each other, each tubular member being detached, and spaced apart, from adjacent tubular members; and the plurality of tubular members may be embedded with a layer of a deformable and expandable plastic material. The plastic material may be silicone, polytetrafluoroethylene, expanded polytetrafluoroethylene, or expanded polyurethane.

Another feature of the present invention is that the first and second tubular members may be connected to the first and second tubes by embedding a portion of the second ends of the first and second tubular members in the deformable and expandable plastic of the tube to which it is to be connected.

An additional feature of the present invention is that each tube may be formed of a plurality of expandable, and deformable tubular members, each tubular member having a longitudinal axis with a plurality of tubular members being aligned with their longitudinal axes being substantially parallel with each other; each tubular member being spaced apart from adjacent tubular members with a single, flexible connector member being disposed between adjacent tubular members; and the plurality of tubular members may be embedded within a layer of a deformable and expandable material. A further feature of the present invention is that the first and second tubular members may be connected to the first and second tubes by embedding a portion of the second ends of the first and second tubular members in the deformable and expandable plastic material of the tube to which it is to be connected.

In accordance with the present invention, the foregoing advantages have also been achieved through the present apparatus for repairing an abdominal aortic aneurysm in an aorta having two iliac arteries associated therewith. The present invention includes: first and second tubes, each tube having first and second ends and a wall surface disposed between the two ends; first and second expandable and deformable tubular members, each expandable and deformable tubular members having first and second ends and a smooth outer wall surface disposed between the first and second ends, the first end of a tube being secured to a second end of a tubular member, the expansion and deformation of the tubular members being controllable; and two catheters, each catheter having an expandable, inflatable portion associated therewith, the tubular members being releasably mounted upon the inflatable portion of each catheter, whereby upon inflation of the expandable, inflatable portion of each catheter, the tubular members are forced radially and outwardly into contact with the aorta and each other to remain secured thereto, whereby the tubes, secured to the tubular members, provide a bilateral passageway through the abdominal aortic aneurysm.

A further feature of the present invention is that each tube may be formed of a plurality of expandable and deformable, tubular members, each tubular member having a longitudinal axis, the plurality of tubular members being aligned with their longitudinal axes being substantially parallel with each other, each tubular member being detached, and spaced apart, from adjacent tubular members; and the plurality of tubular members may be embedded within a layer of a deformable and expandable plastic material. An additional feature of the present invention is that the expandable, inflatable portion of each catheter may extend along a portion of the length of each catheter a distance greater than the combined length of each tube and tubular member, whereby upon expansion and inflation of each expandable, inflatable portion of each catheter, each tubular member and its connected tube are simultaneously expanded.

The bilateral intra-aortic bypass graft for intraluminal delivery, and method and apparatus for repairing an abdominal aortic aneurysm of the present invention, when compared to previously proposed prior art grafts and methods and apparatus for repairing aneurysms, are believed to have the advantages of: a lower mortality rate; shortened recovery periods; not requiring suturing a graft to the aorta; utilizing the existing aortic wall and thrombosis therein to support and reinforce the aortic graft; being suitable for use with patients having other chronic illnesses; being less susceptible to kinking and/or twisting of the graft and permitting the use of a small diameter delivery system.

BRIEF DESCRIPTION OF THE DRAWINGS

In the drawings:

FIG. 1 is a partial cross-sectional view of an abdominal aortic aneurysm in the process of being repaired in accordance with the present invention;

FIG. 2 is partial cross-sectional view of an aorta, abdominal aortic aneurysm, and iliac aneurysm, in the process of being repaired in accordance with the present invention;

FIG. 3 is a partial cross-sectional view of a portion of the aorta of FIG. 1, illustrating a tubular member in the process of being expanded within the aorta;

FIG. 4 is a partial cross-sectional view of the aorta of FIG. 3, illustrating a tubular member being fully expanded;

FIG. 5 is a partial cross-sectional view of the abdominal aortic aneurysm of FIG. 2, illustrating the expansion of the bilateral intra-aortic bypass graft of the present invention;

FIG. 6 is a cross-sectional view taken along line 6—6 of FIG. 5;

FIG. 7 is a cross-sectional view taken along line 7—7 of FIG. 5; and

FIG. 8 is a cross-sectional view taken along line 8—8 of FIG. 5

FIG. 15 is a partial cross-sectional view of another embodiment of a bilateral intra-aortic bypass graft of the present invention;

Figure 9:
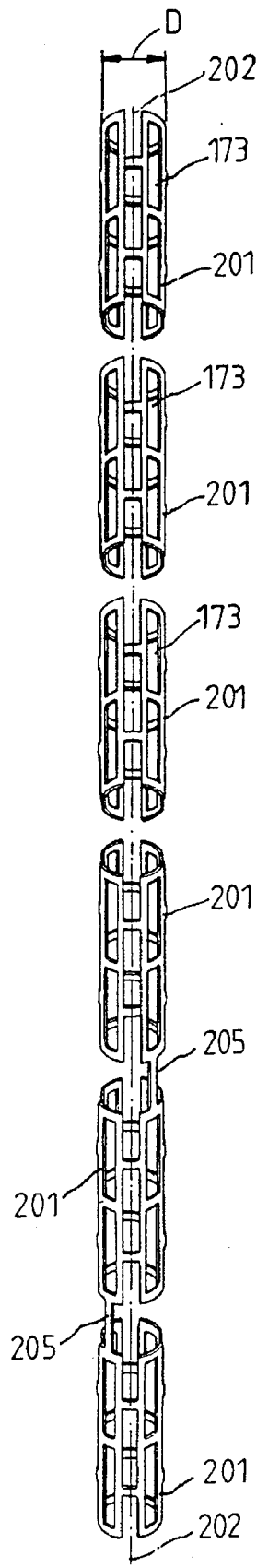
FIG. 9 is a perspective view of a portion of a tube which forms a part of the bilateral intra-aortic bypass graft of the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIGS. 1, 2, 5 a bilateral intra-aortic bypass graft 150 for intraluminal delivery to repair an abdominal aortic aneurysm 151 in an aorta 152 having two iliac arteries 153L, 153R associated therewith is illustrated. Bilateral intra-aortic bypass graft 150, as well as other grafts to be hereinafter described, could also be utilized in the thoracic aorta, and can be used to repair thoracic aneurysms or thoracic dissecting aneurysms. Accordingly, use of the term "aortic aneurysm" in this specification and claims is intended to relate to and mean both abdominal aortic aneurysms and thoracic aneurysms. Aneurysm 151 includes areas of thrombosis 154, which are disposed against the interior wall surface 155 of aorta 152. Blood flows through the aorta in the direction of arrows 156. Associated with aorta 152, above aneurysm 151, are a plurality of renal arteries 157, in fluid communication with aorta 152.

Figure 11:
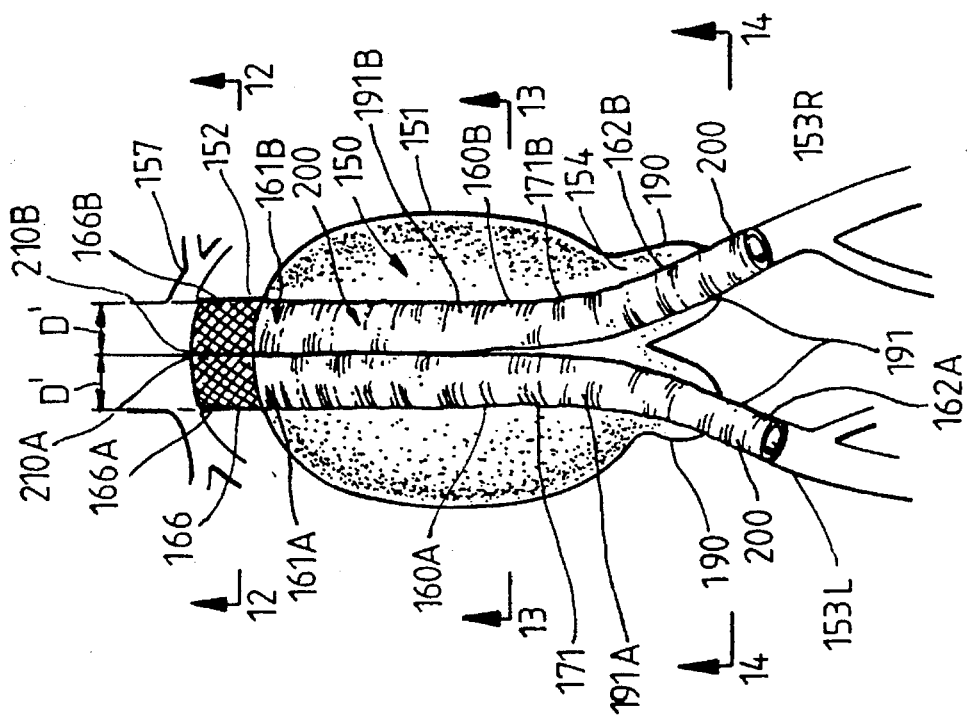
FIG. 11 is a partial cross-sectional view of the aorta and abdominal aortic aneurysm of FIG. 2, illustrating the bilateral intra-aortic bypass graft of the present invention in place in the aorta and abdominal aneurysm.

With reference to FIGS. 1, 5, and 11, bypass graft 150 is seen to generally comprise: a first tube 160A having first and second ends 161A, 162A and wall surface 163A disposed between the two ends 161A, 162A, at least a portion of the tube 160A adapted to be disposed within the aneurysm 151; a second tube 160B having first and second ends 161B, 162B and a wall surface 163B disposed between the two ends 161B, 162B, at least a portion of the tube 160B adapted to be disposed within the aneurysm 151; and means for securing 165 the first ends 161A, 161B of the first and second tubes 160A, 160B to the aorta 152, the securing means including first and second tubular members 166A, 166B, each tubular member 166A, 166B having first and second ends 167A, 167B, 168A, 168B, the first tube 160A being connected to the first tubular member 166A, and the second tube 160B being connected to the second tubular member 166B. It should be noted that like reference numerals are utilized throughout this Detailed Description of the Invention, with different letter subscripts to identify components of the present invention which are identical in construction to each other, in that many components of the present invention are a mirror image of adjacent components.

Still with reference to FIGS. 1, 5, and 11, preferably, the tubular members 166A, 166B, of securing means 165 have a first diameter D (FIGS. 1 and 2), which permits intraluminal delivery of the tubular members 166A, 166B into the aorta 152. Upon the application from the interior of the tubular members 166A, 166B of a radially, outwardly extending force, as will be hereinafter described in greater detail, the tubular members 166A, 166B, have a second, expanded and deformed diameter D' (FIGS. 5 and 11), the second diameter D' being variable and dependent upon the amount of force applied to the tubular members 166A, 166B, whereby the tubular members 166A, 166B, may be expanded and deformed to secure the first ends 167A, 167B of the tubular members 166A, 166B to the aorta 152, and a bilateral passageway 200 (is formed within the abdominal aortic aneurysm 151) by passageways 191A, 191B extending through the tubular members 166 and tubes 160. Preferably, as seen in FIGS. 5 and 11, at least a portion of the first and second tubes 160A, 160B is in an abutting relationship, the abutting portions of the first and second tubes 160A, 160B, being generally disposed toward the upper ends 161A, 161B of tubes 160A, 160B, whereby bilateral intra-aortic bypass graft 150, after implantation within aorta 152 and aneurysm 151, generally has an inverted Y-shaped configuration, as illustrated in FIGS. 5 and 11. Additionally, after tubular members 166A, 166B have been expanded and have their second, expanded and deformed diameter D', at least a portion, and preferably all of, the first and second tubular members 166A, 166B, are in an abutting relationship, as seen in FIGS. 5 and 11.

With reference to FIG. 1, each tubular member 166A, 166B preferably has a smooth outer wall surface 169A, 169B disposed between its first and second ends 167A, 167B, 168A, 168B. Wall surfaces 169A, 169B, preferably have a substantially uniform thickness with a plurality of slots 173 formed therein, the slots 173 being disposed substantially parallel to the longitudinal axes of the tubular members 166A, 166B. It has been found that one type of tubular member 166, which is particularly useful as securing means 165 are the expandable intraluminal grafts disclosed in U.S. Pat. No. 4,733,665, issued Mar. 29, 1988; U.S. Pat. No. 4,739,762, issued Apr. 26, 1988; and U.S. Pat. No. 4,776,337, issued Oct. 11, 1988, all of the foregoing patents being in the name of Julio C. Palmaz, and assigned to Expandable Grafts Partnership. Each of these patents is incorporated herein by reference. Other tubular members 166 could be utilized as securing means 165, provided they have the ability to be controllably expanded and deformed from the first diameter D, which permits intraluminal delivery of securing means 165, to the second expanded and deformed diameter D', in order to secure the tubular members 166A, 166B, and their connected tubes 160A, 160B within aorta 152.

With reference to FIGS. 1 and 11, tubes 160A, 160B preferably have a generally, circular cross-sectional configuration, and tubes 160A, 160B made be made from a variety of materials, provided they have the requisite strength characteristics to be utilized as a bypass graft 150, as well as have the requisite compatibility with the human body in order to be used as a graft, or implant material, without being rejected by the patient's body. Examples for such materials are DACRON® and other polyester materials, TEFLON® (polytetrafluoroethylene), TEFLON® coated DACRON®, porous polyurethane, silicone, expanded polytetrafluoroethylene, and expanded polyurethane. It is preferred that all of the foregoing materials be porous to allow for an intimal layer to form on the tubes 160. Additionally, tubes 160A, 160B can be made by the replamineform replicated life forms process, which is a method for fabricating uniformly microporous materials from marine skeletal structures. The foregoing described fabric materials can be knitted or woven, and can be warp or weft knitted. If the material is warp knitted, it may be provided with a velour, or towel like surface, which speeds up clotting of blood which contacts tubes 160A, 160B in order to increase the attachment, or integration, of tubes 160A, 160B to aorta 152, or to assist the integration of tubes 160A, 160B to the thrombosis 154. Tubes 160A, 160B can also be made of a bio-erodible, or degradable material, such as albumin or collagen or a collagen coated material. A tube 160 which is bio-erodible, would erode and dissolve, or degrade, over a period of time; however, it is believed that a layer of endothelium, or skin, will grow as the tubes 160A, 160B erode, the new layers of endothelium, or skin, provide a new, fluid impervious lining within aneurysm 151. In some procedures, it might be desirable to make tubes 160A, 160B of a fluid impervious material. Additionally, tubes 160A, 160B, as well securing means 165, or tubular members 166A, 166B, could have a coating of a biologically inert material, such as TEFLON® or porous polyurethane.

If any of the foregoing described materials are used for the manufacture of tubes 160A, 160B, the first ends 161A, 161B of tubes 160A, 160B may be connected to the second ends 168A, 168B of the tubular members 166A, 166B, as by a plurality of conventional sutures of polypropylene, DACRON®, or any other suitable material. Preferably, the ends 161A, 161B of tubes 160A, 160B overlap and cover the second ends 168A, 168B of tubular members 166A, 166B, such overlapping being approximately 50% of the length of tubular 166A, 166B. The first ends 161A, 161B of tubes 160A, 160B, which overlap the second ends 168A, 168B of tubular members 166A, 166B, are preferably constructed so that they are radially expandable, whereby the first ends 161A, 161B of tubes 160A, 160B can conform with the second, expanded and deformed diameter D' of the second ends 168A, 168B of the tubular members 166A, 166B. If tubes 160A, 160B are woven, the weave of the materials at its first ends 161A, 161B is looser, so that the desired radial expansion can be obtained. The intermediate portions 171A, 171B (FIG. 11) of tubes 160A, 160B disposed between first and second ends 161A, 161B, 162A, 162B thereof, are preferably not substantially radially expandable when tubes 160A, 160B are manufactured from the foregoing described fabric, or fabric like, materials.

Figure 10A:
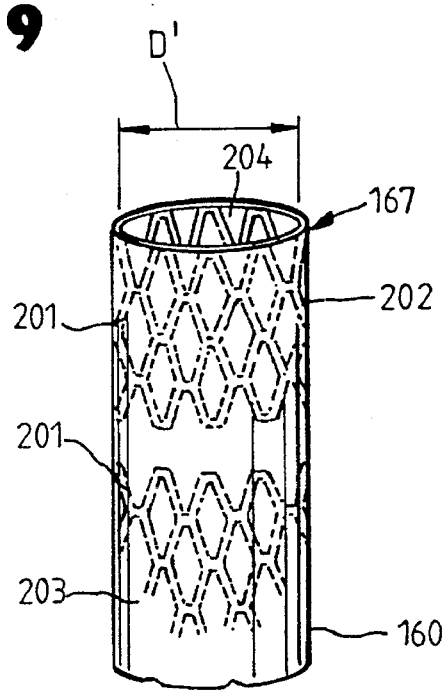
FIG. 10A is a partial, perspective view of a portion of the bilateral intra-aortic bypass graft of the present invention.
Figure 10B:
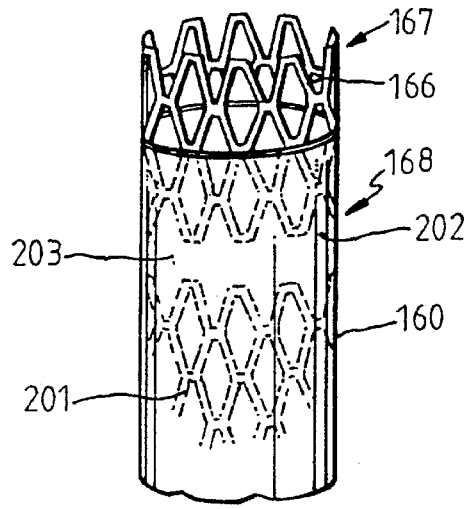
FIG. 10B is a partial, perspective view of a portion of the bilateral intra-aortic bypass graft of the present invention.

With reference to FIGS. 9, 10A and 10B, another embodiment of tubes 160 of bypass graft 150 are illustrated. Each tube 160A, 160B is preferably formed of a plurality of expandable and deformable, tubular members 201. Each tubular member 201 has a longitudinal axis, with a plurality of tubular members 201 being aligned with their longitudinal axes being substantially parallel with each other, as illustrated by center line 202. Each tubular member 201 is detached, and spaced apart, from adjacent tubular members 201. Tubular members 201 are of the same construction of tubular members 166 previously described, however, the length of tubular members 201 and number of slots 173 extending along the length of each tubular member 201 may be varied depending upon the total length of tube 160. After the plurality of tubular members 201 have been aligned as illustrated in FIG. 9, with tubular members 201 being disposed with their first unexpanded diameter D which permits intraluminal delivery of the tubular members 201, the plurality of tubular members 201 are disposed in a suitable, conventional jig, die, or mold. The plurality of tubular members 201 are then embedded within a layer 202 of a deformable and expandable plastic material, such embedding being carried out through use of any conventional molding process. The plastic material may be silicone, polytetrafluoroethylene, expanded polytetrafluoroethylene, expanded polyurethane, or any other plastic material have the requisite strength characteristics to be utilized as a bypass graft, as well as have the requisite compatibility with the human body in order to be used as a graft, or implant material, without being rejected by the patient's body, as well as have the ability to expand as tubular members 201 are expanded, as will be hereinafter described, and be able to maintain the expanded configuration when tubular members 201 have a second, expanded and deformed diameter D' as illustrated in FIG. 10A.

The resulting tube 160, after the plurality of tubular members 201 have been embedded within the layer 202 of plastic material, is a tube 160 having a substantially smooth inner and outer surface 203, 204 formed by the layer 202 of plastic material in which tubular members 201 are embedded. It is believed that such tubes 160 will be substantially non-collapsible and not subject to kinking and/or twisting upon being implanted.

Tube 160 of FIG. 10A may be connected to the second end 168 of tubular member 166 in the manner previously described, such as by a plurality of conventional sutures; however, preferably the first and second tubular members 166A, 166B are connected to the first and second tubes 160A, 160B by embedding a portion of the second ends 168A, 168B of the first and second tubular members 160A, 160B in the plastic material 202 of the tube 160 to which tubular members 166A, 166B are to be connected, as illustrated in FIG. 10B. As seen in FIG. 10B, the upper end 167, or leading edge, of tubular member 166 is exposed for direct contact with aorta 152 and its adjacent tubular member 166, as illustrated in FIGS. 10B, 5, and 11. The lower end 168, or trailing edge, of tubular member 166 being embedded within the layer 202 of plastic material, and spaced apart, and detached from the uppermost tubular member 201, as illustrated in FIG. 10A.

Still with reference to FIG. 9, alternatively each tubular member 201 may be spaced apart from adjacent tubular members 201 and connected by a single, flexible connector member 205, two such flexible connector members being illustrated, and the plurality of connected tubular members 201 are then embedded within the layer 202 of the deformable and plastic material. It is believed that one type of flexible connector member which may be particularly useful as connector members 205 are those illustrated in U.S. patent application Ser. No. 174,246, filed Mar. 28, 1988, and U.S. patent application Ser. No. 657,296, filed Feb. 19, 1991, both of these application being assigned to Expandable Grafts Partnership. Each of these applications is incorporated herein by reference. Other connector members 205 could be utilized, provided they have the ability to permit tubes 160 of FIGS. 10A and 10B, to be implanted as will be hereinafter described in greater detail, and to be intraluminally delivered to the aorta 152 which would require tube 160 to be flexible and capable of bending and flexing so as to negotiate through the curved veins, arteries, and/or body passageways toward the aorta 152.

With reference to FIG. 15, another embodiment of bilateral intra-aortic bypass graft 150 is illustrated. Graft 51' includes means for securing 192 the lower ends 162A, 162B of tubes 160A, 160B to the two iliac arteries 153. Securing means 192 preferably includes a third expandable and deformable tubular member 166A' connected to the second end 162 of the first tube 160A, and a fourth expandable and deformable, tubular member 166B' connected to the second end 162B of the second tube 160A. Preferably, third and fourth members 166A', 166B' are of the same type of construction as those used for securing means 165, or tubular members 166A, 166B. Third and fourth tubular members 166A', 166B' may be connected to the lower ends 162A, 162B of tubes 160A, 160B, as by means of sutures, previously described, when tubes 160A, 160B are of fabric, or similar construction, as previously described. Alternatively, if tubes 160A, 160B, have the construction as illustrated in FIGS. 9, 10A, and 10B, third and fourth tubular members 166A', 166B' may be also connected as by conventional sutures, as previously described, or preferably may be secured to the lower ends 162A, 162B of tubes 160A, 160B, by embedding a portion of the first ends 167A, 167B of tubular members 166A', 166B' in the deformable and expandable plastic material 202 disposed at the second ends 162A, 162B of tubes 160A, 160B as previously described in connection with FIG. 10B. As will be hereinafter described in further detail, securing means 192, or third or fourth tubular members 166A', 166B', may be expanded and deformed in the same manner as securing means 165 to force the third and fourth tubular members 166A', 166B' into contact with an iliac artery, 153L, 153R. Although the flow of pumped blood downwardly through aorta 152 and into iliac arteries 153L, 153R is believed to provide enough pressure to maintain bilateral passageways 191A, 191B, formed by tubes 160A, 160B, in their desired positions within iliac arteries 153L, 153R, as illustrated in FIGS. 11 and 15, there is a slight negative vacuum pressure component associated with the pumping pressure, whereby the securing means 192 might be required. Securing means 192 also serves to ensure no movement of passageways 191A, 191B, caused by a person's body movements.

With reference to FIGS. 1, 2, and 5, the method and apparatus for repairing an abdominal aortic aneurysm of the present invention will be described. Apparatus 180 for repairing an abdominal aortic aneurysm 151 generally comprises: first and second tubes 160A, 160B and first and second expandable and deformable tubular members 166A, 166B, tubular members 166 and tubes 160 being constructed as previously described; and two catheters 181A, 181B, ,each catheter have an expandable, inflatable portion 182A, 182B, or balloon 183 associated therewith and a nosepiece 184. The tubular members 166A, 166B are releasably mounted to the inflatable portion 182 of each catheter 181, in any suitable fashion, whereby upon inflation of the expandable, inflatable portion 182 of each catheter 181A, 181B, the tubular members 166A, 166B are forced radially outwardly into contact with the aorta 152 and with each other to remain secured to aorta 152, whereby the tubes 160A, 160B, secured to the tubular members 166A, 166B, provide a bilateral passageway 200, or bilateral passageways 191A, 191B (FIGS. 11 and 15) through the abdominal aortic aneurysm 151.

The apparatus 180 for repairing the abdominal aortic aneurysm 151 as illustrated in FIGS. 1 and 2, is in its configuration it would have for intraluminal delivery into aorta 152 and aneurysm 151. Preferably, the first tube 160A, tubular member 166A, and catheter 181A are intraluminally delivered through a first femoral artery; and the second tube 160B, tubular member 166B, and catheter 181B are intraluminally delivered through a second femoral artery and in turn each pass through an iliac artery 153L, 153R, as illustrated in FIG. 2. In the configuration shown in FIGS. 1 and 2, the tubular members 166A, 166B have their first unexpanded, undeformed diameter D. In FIG. 5, tubular members 166A, 166B, have been expanded and deformed into their second, expanded and deformed diameter D'.

Expansion and deformation of tubular members 166A, 166B is controlled by the expansion of balloons 183 of catheters 181A, 181B in a conventional manner. When apparatus 180 is being intraluminally delivered, catheters 181A, 181B, tubular members 166A, 166B, and tubes 160A, 160B are preferably enclosed by conventional catheter sheathes 186A, 186B which are removed, as shown in FIG. 1, as apparatus 180 is disposed in its desired location within aorta 152.

If tubular members 166A, 166B, are utilized in connection with a fabric type tube 160, as previously described, balloon 183 of catheter 181 may have a length which extends from slightly beyond the first end 167 of tubular member 166, and to a position slightly beyond the second end 168 of tubular member 166. As illustrated in FIG. 5, if apparatus 180 includes tubes 160 constructed in a manner as described in FIGS. 9, 10A, and 10B, inflatable portion 182, or balloon 183 associated with each catheter 181 extends along a portion of the length of each catheter a distance greater than the combined length tube 160 and its associated tubular member 166, as illustrated in FIG. 5. Thus, upon expansion and inflation of each expandable and inflatable portion 182, or balloon 183, associated with each catheter 181, each tubular member 166A, 166B, is simultaneously expanded along with its connected tube 160A, 160B, including the plurality of tubular members 201 embedded within the layer 202 of plastic material of tubes 160A, 160B (FIGS. 9, 10A, 10B). Deflation of balloons 183 permits the withdrawal of catheters 181 and release of balloons 183 and catheters 181 from bypass graft 150 after graft 150 has been disposed in the configuration illustrated in FIG. 5. When tubes 160 are utilized of the construction illustrated in FIGS. 9, 10A, 10B, as shown in FIG. 5, the resulting bilateral passageway 191 formed in aorta 152 and aneurysm 151 is believed to be substantially non-collapsible, because of the presence of the plurality of tubular members 201 embedded within tubes 160A, 160B.

When implanting a bypass graft 150 of the construction illustrated in FIG. 15, first, second, third, and fourth tubular members 166A, 166B, 166A', 166B' may be simultaneously expanded and deformed into the expanded configuration illustrated in FIG. 5, as by use of the catheters 182 illustrated in FIG. 5, along with tubes 160A, 160B.

As illustrated in FIGS. 1, 2, 5, and 6, tubular members 166A, 166B, are initially disposed within aorta 152 substantially even and on the same level as each other, at which time sheathes 186 are removed and balloons 183A, 183B are simultaneously expanded as illustrated in FIGS. 5 and 6, until tubular members 166A, 166B are in an abutting relationship with each other and against aorta 150. Upon final inflation and expansion of the balloons 183A, 183B to force tubular members 166A, 166B into their final configuration illustrated in FIGS. 11 and 12, the abutting portions 210A, 210B of tubular members 166A, 166B, are flattened against each other into the configuration shown in FIG. 12, whereby the initially present gaps 211 (FIG. 6) between adjacent tubular members 166A, 166B, are closed off and removed.

Figure 13:
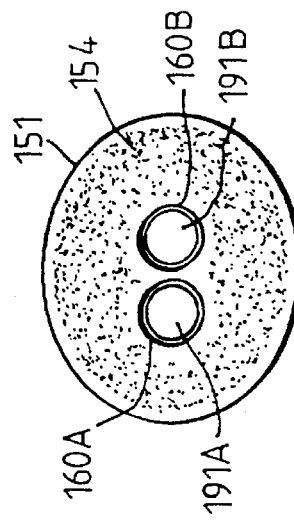
FIG. 13 is a cross-sectional view taken along line 13—13 of FIG. 11.
Figure 14:
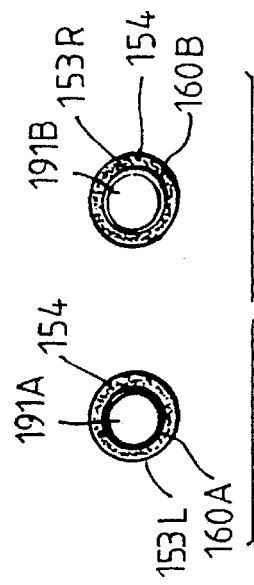
FIG. 14 is a cross-sectional view taken along line 14—14 of FIG. 11.

FIGS. 13 and 14 illustrate bypass graft 150 after it has been implanted for a period of time, whereby the aneurysm 151 has thrombosed about tubes 160A, 160B and into contact therewith, and bilateral passageways 191A, 191B are thus disposed within aneurysm 151.

Figure 12:
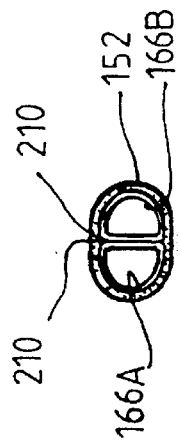
FIG. 12 is a cross-sectional view taken along line 12—12 of FIG. 11.

With reference to FIGS. 3 and 4, an alternative method for repairing an abdominal aortic aneurysm in an aorta 152 is illustrated. In this embodiment, bilateral intra-aortic bypass graft 150 includes a fifth expandable and deformable tubular member 166C of the same construction of the first through fourth tubular members 166A, 166B, 166A', 166B' as previously described. Prior to the intraluminal delivery of tubular members 166A, 166B, and tubes 160A, 160B as previously described in connection with FIGS. 1, 2, and 5, the fifth tubular member 166C is intraluminally delivered by a third catheter 181' and expanded from its first diameter D" to its second, expanded and deformed diameter D''', as illustrated in FIG. 4, to secure the fifth tubular member 166C within the aorta. After the fifth expandable tubular member 166C has been implanted within aorta 152, as shown in dotted lines in FIG. 1, the remaining elements of bypass graft 150 are implanted within aorta 152 and aneurysm 151 as previously described in connection with FIGS. 1, 2, and 5. Upon expansion of first and second tubular members 166A, 166B, as previously described, those tubular members 166A, 166B, will be in abutting relationship with each other, as illustrated in FIG. 12, and will also be secured within aorta 152, via their expansion and deformation, into contact with fifth tubular member 166C which is secured in aorta 152.

It is believed that the use of fifth tubular member 166C will provide adequate anchorage for the tubular members 166A, 166B of bypass graft 150, and equalize forces exerted upon aorta 152 by the expansion of tubular members 166A, 166B. Fifth tubular member 166C has a final expanded diameter D''' which is approximately twice the size of the expanded diameter D' of tubular members 166A, 166B. Because fifth tubular member 166C does not have a tube 160 attached thereto, its delivery system, or catheter 181' and sheath 186' can be smaller, and they can be intraluminally delivered without any of the previously described disadvantage associated with prior art aortic grafts, having a large diameter tube connected thereto.

It is to be understood that the invention is not limited to the exact details of construction, operation, exact materials or embodiments shown and described, as obvious modifications and equivalents will be apparent to one skilled in the art. For example, the expandable, inflatable portions of the catheters could be a plurality of hydraulically actuated rigid members disposed on a catheter or a plurality of balloons could be utilized to expand the securing means. Additionally, the wall surfaces of the tubular members could be formed by a plurality of wires having a smooth exterior surface. The tubes could also be used individually as grafts for other body passageways. Accordingly, the invention is therefore to be limited only by the scope of the appended claims.

We claim:

1. A bilateral intra-aortic bypass graft for intraluminal delivery to repair an abdominal aortic aneurysm in an aorta having a diameter and two iliac arteries associated therewith, by forming a bilateral passageway through the abdominal aortic aneurysm, comprising:

a first tube having a diameter, first and second ends and a wall surface disposed between the two ends, at least a portion of the first tube adapted to be disposed within the abdominal aortic aneurysm;

a second tube having a diameter, first and second ends and a wall surface disposed between the two ends, at least a portion of the second tube adapted to be disposed within the abdominal aortic aneurysm; and means for securing the first ends of the first and second tubes in an abutting relationship in the aorta, the securing means including first and second tubular members, each tubular member having first and second ends, the first tube being connected to the first tubular member and the second tube being connected to the second tubular member, the tubular members having a first diameter which permits intraluminal delivery of the tubular members and tubes into the aorta and the tubular members each having a second, expanded and deformed diameter, with at least a portion of the first and second tubular members in an abutting relationship, upon the application from the interior of the tubular members of a radially, outwardly extending force, to expand and deform the tubular members to secure the first ends of the tubular members to the aorta in an abutting relationship and to form a bilateral passageway within the abdominal aortic aneurysm.

2. The bilateral intra-aortic bypass graft of claim 1, wherein at least a portion of the first and second tubes are in an abutting relationship with each other when the first and second tubular members have their second, expanded and deformed diameter.

3. The bilateral intra-aortic bypass graft of claim 1, wherein each tubular member has a smooth outer wall surface disposed between its first and second ends, the wall surfaces having a substantially uniform thickness and a plurality of slots formed therein, the slots being disposed substantially parallel to the longitudinal axes of the tubular members, a first end of a tube being secured to a second end of a tubular member.

4. The bilateral intra-aortic bypass graft of claim 1, wherein a biologically inert coating is disposed on the tubes.

5. The bilateral intra-aortic bypass graft of claim 1, wherein the tubes are made of a material which is impervious to the flow of fluid.

6. The bilateral intra-aortic bypass graft of claim 1, wherein the tubes are made of a material which is bio-erodible.

7. The bilateral intra-aortic bypass graft of claim 1, wherein a third expandable and deformable, tubular member is connected to the second end of the first tube; a fourth expandable and deformable, tubular member is connected to the second end of the second tube; and the third and fourth tubular members are expanded and deformed to force the third and fourth tubular members radially outwardly into contact with an iliac artery.

8. The bilateral intra-aortic bypass graft of claim 1, wherein each tube is formed of a plurality of expandable and deformable, tubular members, each tubular member having a longitudinal axis, the plurality of tubular members being aligned with their longitudinal axes being substantially parallel with each other, each tubular member being detached, and spaced apart, from adjacent tubular members; and the plurality of tubular members are embedded within a layer of a deformable and expandable plastic material.

9. The bilateral intra-aortic bypass graft of claim 8, wherein the plastic material is silicone.

10. The bilateral intra-aortic bypass graft of claim 8, wherein the plastic material is polytetrafluoroethylene.

11. The bilateral intra-aortic bypass graft of claim 10, wherein the plastic material is expanded polytetrafluoroethylene.

12. The bilateral intra-aortic bypass graft of claim 8, wherein the plastic material is expanded polyurethane.

13. The bilateral intra-aortic bypass graft of claim 8, wherein the first and second tubular members are connected to the first and second tubes by embedding a portion of the second ends of the first and second tubular members in the deformable and expandable plastic material of the tube to which it is to be connected.

14. The bilateral intra-aortic bypass graft of claim 1, including a fifth expandable and deformable tubular member, wherein the first and second tubular members are disposed within the fifth expandable tubular member in an abutting relationship with each other and with the fifth expandable tubular member, whereby the first and second tubular members may be secured within the aorta and within the fifth tubular member.

15. The bilateral intra-aortic bypass graft of claim 1, wherein each tube is formed of a plurality of expandable and deformable tubular members, each tubular member having a longitudinal axis with the plurality of tubular members being aligned with their longitudinal axes being substantially parallel with each other; each tubular member being spaced apart from adjacent tubular members with a single, flexible connector member being disposed between adjacent tubular members; and the plurality of tubular members are embedded within a layer of a deformable and expandable plastic material.

16. The bilateral intra-aortic bypass graft of claim 15, wherein the plastic material is silicone.

17. The bilateral intra-aortic bypass graft of claim 15, wherein the plastic material is polytetrafluoroethylene.

18. The bilateral intra-aortic bypass graft of claim 17, wherein the plastic material is expanded polytetrafluoroethylene.

19. The bilateral intra-aortic bypass graft of claim 15, wherein the plastic material is expanded polyurethane.

20. The bilateral intra-aortic bypass graft of claim 15, wherein the first and second tubular members are connected to the first and second tubes by embedding a portion of the second ends of the first and second tubular members in the deformable and expandable plastic material of the tube to which it is to be connected.

21. The bilateral intra-aortic bypass graft of claim 1, wherein the tubes are made of a synthetic polyester material.

22. The bilateral intra-aortic bypass graft of claim 1, wherein the tubes are made of polytetrafluoroethylene.

23. An apparatus for repairing an abdominal aortic aneurysm in an aorta having a diameter and two iliac arteries associated therewith, by forming a bilateral passageway through the abdominal aortic aneurysm, comprising:

(a) first and second tubes, each tube having a diameter, first and second ends and a wall surface disposed between the two ends;

(b) first and second expandable and deformable tubular members, each expandable and deformable tubular member, having first and second ends and a smooth outer wall surface disposed between the first and second ends, the first end of a tube being secured to a second and of a tubular member, the expansion and deformation of the tubular members being controllable; and (c) two catheters, each catheter having an expandable, inflatable portion associated therewith, the tubular members being releasably mounted upon the inflatable portions of each catheter, whereby upon inflation of the expandable, inflatable portion of each catheter, the tubular members are forced radially outwardly into contact in an abutting relationship with the aorta and each other to remain secured thereto, whereby the tubes, secured to the tubular members, provide a bilateral passageway through the abdominal aortic aneurysm.

24. The apparatus of claim 23, wherein each tube is formed of a plurality of expandable and deformable, tubular members, each tubular member having a longitudinal axis, the plurality of tubular members being aligned with their longitudinal axes being substantially parallel with each other, each tubular member being detached, and spaced apart, from adjacent tubular members; and the plurality of tubular members are embedded within a layer of a deformable and expandable plastic material.

25. The apparatus of claim 24, wherein the expandable, inflatable portion of each catheter extends along a portion of the length of each catheter for a distance greater than the combined length of each tube and tubular member, whereby upon expansion and inflation of each expandable, inflatable portion of each catheter, each tubular member and its connected tube are simultaneously expanded.

26. The apparatus of claim 23, wherein each tube is formed of a plurality of expandable and deformable tubular members, each tubular member having a longitudinal axis with the plurality of tubular members being aligned with their longitudinal axes being substantially parallel with each other; each tubular member being spaced apart from adjacent tubular members with a single, flexible connector member being disposed between adjacent tubular members; and the plurality of tubular members are embedded within a layer of a deformable and expandable plastic material.

27. The apparatus of claim 26, wherein the expandable, inflatable portion of each catheter extends along a portion of the length of each catheter for a distance greater than the combined length of each tube and tubular member, whereby upon expansion and inflation of each expandable, inflatable portion of each catheter, each tubular member and its connected tube are simultaneously expanded.

28. A bilateral bypass graft for a body passageway, having a diameter, for intraluminal delivery to repair the body passageway by forming a bilateral passageway through the body passageway, comprising:

a first tube having a diameter, first and second ends and a wall surface disposed between the two ends, at least a portion of the first tube adapted to be disposed within the body passageway;

a second tube having a diameter, first and second ends and a wall surface disposed between the two ends, at least a portion of the second tube adapted to be disposed within the body passageway; and means for securing the first ends of the first and second tubes in an abutting relationship in the body passageway, the securing means including first and second tubular members, each tubular member having first and second ends, the first tube being connected to the first tubular member and the second tube being connected to the second tubular member, the tubular members having a first diameter which permits intraluminal delivery of the tubular members and tubes into the body passageway and the tubular members each having a second, expanded and deformed diameter, with at least a portion of the first and second tubular members in an abutting relationship, upon the application from the interior of the tubular members of a radially, outwardly extending force, to expand and deform the tubular members to secure the first ends of the tubular members to the body passageway in an abutting relationship and to form a bilateral passageway within the body passageway.

29. The bilateral bypass graft of claim 28, wherein at least a portion of the first and second tubes are in an abutting relationship with each other when the first and second tubular members have their second, expanded and deformed diameter.

30. The bilateral bypass graft of claim 28, wherein each tubular member has a smooth outer wall surface disposed between its first and second ends, the wall surfaces having a substantially uniform thickness and a plurality of slots formed therein, the slots being disposed substantially parallel to the longitudinal axes of the tubular members, a first end of a tube being secured to a second end of a tubular member.

31. The bilateral bypass graft of claim 28, wherein a biologically inert coating is disposed on the tubes.

32. The bilateral bypass graft of claim 28, wherein the tubes are made of a material which is impervious to the flow of fluid.

33. The bilateral bypass graft of claim 28, wherein the tubes are made of a material which is bio-erodible.

34. The bilateral bypass graft of claim 28, wherein the tubes are made of a synthetic polyester material.

35. The bilateral bypass graft of claim 28, wherein the tubes are made of polytetrafluoroethylene.

36. The bilateral bypass graft of claim 28, wherein a third expandable and deformable, tubular member is connected to the second end of the first tube; a fourth expandable and deformable, tubular member is connected to the second end of the second tube; and the third and fourth tubular members are expanded and deformed to force the third and fourth tubular members radially outwardly into contact with the body passageway.

37. The bilateral bypass graft of claim 28, wherein each tube is formed of a plurality of expandable and deformable, tubular members, each tubular member having a longitudinal axis, the plurality of tubular members being aligned with their longitudinal axes being substantially parallel with each other, each tubular member being detached, and spaced apart, from adjacent tubular members; and the plurality of tubular members are embedded within a layer of a deformable and expandable plastic material.

38. The bilateral intra-aortic bypass graft of claim 37, wherein the plastic material is silicone.

39. The bilateral bypass graft of claim 32, wherein the plastic material is polytetrafluoroethylene.

40. The bilateral intra-aortic bypass graft of claim 39, wherein the plastic material is expanded polytetrafluoroethylene.

41. The bilateral intra-aortic bypass graft of claim 32, wherein the plastic material is expanded polyurethane.

42. The bilateral intra-aortic bypass graft of claim 32, wherein the first and second tubular members are connected to the first and second tubes by embedding a portion of the second ends of the first and second tubular members in the deformable and expandable plastic material of the tube to which it is to be connected.

43. The bilateral intra-aortic bypass graft of claim 28, including a fifth expandable and deformable tubular member, wherein the first and second tubular members are disposed within the fifth expandable tubular member in an abutting relationship with each other and with the fifth expandable tubular member, whereby the first and second tubular members may be secured within the body passageway and within the fifth tubular member.

44. The bilateral bypass graft of claim 43, wherein each tube is formed of a plurality of expandable and deformable tubular members, each tubular member having a longitudinal axis with the plurality of tubular members being aligned with their longitudinal axes being substantially parallel with each other; each tubular member being spaced apart from adjacent tubular members with a single, flexible connector member being disposed between adjacent tubular members; and the plurality of tubular members are embedded within a layer of a deformable and expandable plastic material.

45. The bilateral bypass graft of claim 44, wherein the plastic material is silicone.

46. The bilateral intra-aortic bypass graft of claim 44, wherein the plastic material is polytetrafluoroethylene.

47. The bilateral intra-aortic bypass graft of claim 46, wherein the plastic material is expanded polytetrafluoroethylene.

48. The bilateral intra-aortic bypass graft of claim 44, wherein the plastic material is expanded polyurethane.

49. The bilateral intra-aortic bypass graft of claim 44, wherein the first and second tubular members are connected to the first and second tubes by embedding a portion of the second ends of the first and second tubular members in the deformable and expandable plastic material of the tube to which it is to be connected.

* * * * *